United States Patent [19]

Shinoki et al.

[11] Patent Number: 5,789,561
[45] Date of Patent: Aug. 4, 1998

[54] FLUORINE-SUBSTITUTED GANGLIOSIDE GM3 DERIVATIVE AND INTERMEDIATES THEREFOR

[75] Inventors: Noriyuki Shinoki; Takao Iida, both of Ibaraki, Japan

[73] Assignee: Daikin Industries Ltd., Osaka, Japan

[21] Appl. No.: 894,132

[22] PCT Filed: Dec. 12, 1996

[86] PCT No.: PCT/JP96/03624

§ 371 Date: Aug. 13, 1997

§ 102(e) Date: Aug. 13, 1997

[87] PCT Pub. No.: WO97/22615

PCT Pub. Date: Jun. 26, 1997

[30] Foreign Application Priority Data

Dec. 18, 1995 [JP] Japan ................................ 7-328754

[51] Int. Cl.$^6$ .................... C07H 15/04; C07H 15/10; A61K 31/70
[52] U.S. Cl. .................... 536/17.9; 536/18.4; 514/25
[58] Field of Search ................ 536/17.9, 18.4; 514/25

[56] References Cited

U.S. PATENT DOCUMENTS

| | | | |
|---|---|---|---|
| 4,675,287 | 6/1987 | Reisfeld et al. | 435/7 |
| 5,350,841 | 9/1994 | Romeo et al. | 536/53 |
| 5,583,208 | 12/1996 | Iida et al. | 536/17.9 |
| 5,627,290 | 5/1997 | Iida et al. | 549/419 |

FOREIGN PATENT DOCUMENTS 728763  8/1996  European Pat. Off. .

*Primary Examiner*—Kathleen K. Fonda
*Attorney, Agent, or Firm*—Birch, Stewart, Kolasch & Birch, LLP

[57] ABSTRACT

A novel fluorine-substituted ganglioside GM3 derivative represented by the formula (I):

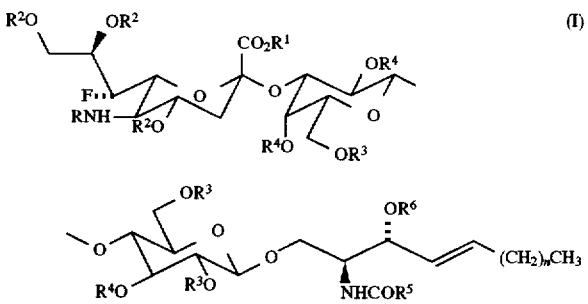

wherein R is an aliphatic acyl group, $R^1$ is a hydrogen atom or a lower alkyl group, $R^2$, $R^3$, $R^4$ and $R^6$ represent independently of one another a hydrogen atom, an aliphatic lower acyl group or an aromatic acyl group, $R^5$ is an straight or branched, saturated or unsaturated aliphatic hydrocarbon group having 1 to 30 carbon atoms, and n is an integer of 0 to 20, provided that when $R^1$ is a hydrogen atom, $R^2$, $R^3$, $R^4$ and $R^6$ are hydrogen atoms, or when $R^1$ is a lower alkyl group, $R^2$, $R^3$, $R^4$ and $R^6$ are each an aliphatic lower acyl group or an aromatic acyl group.

4 Claims, No Drawings

FLUORINE-SUBSTITUTED GANGLIOSIDE GM3 DERIVATIVE AND INTERMEDIATES THEREFOR

This is the U.S. national stage entry under 35 U.S.C. 371 of PCT/JP96/03624, filed Dec. 12, 1996.

FIELD OF THE INVENTION

The present invention relates to a ganglioside GM3 derivative in which a hydroxyl group at the C-7 position of sialic acid is replaced by a fluorine atom and which contributes to various biological phenomena as a biologically active glycolipid, and intermediates therefor.

DESCRIPTION OF THE PRIOR ART

Ganglioside is a collective name of sphingoglucolipids having a sialic acid moiety, and an amphipathic molecule comprising a hydrophilic saccharide chain and a hydrophobic ceramide moiety. Depending on their structures, in particular, kinds of the saccharide structures, they have abbreviations such as GM1, GM2, GM3, GM4, GD2, GD3, GT2, GT3, GT1b; and the like, and they are localized in various tissues as minor components in biomembranes.

In these years, the gangliosides attract attentions, as they are revealed to play a fundamental role as receptor molecules for various cytotoxins, hormones, interferons, neurotransmitters, and influenza viruses (Y. Suzuki, "SEITAI NO KAGAKU" (Science of Living Bodies), 38 (4), 332–339 (1987)).

For example, hemagglutinin and sialidase which identify the saccharide chain containing sialic acid are present on the cell surface of the influenza virus and play an important role in absorption and penetration of the influenza virus in mammal cells. When mechanisms of the absorption and penetration of the influenza virus are viewed from the host side, hemagglutinin and sialidase are important components to prevent infections of the virus (Y. Suzuki, Biochemistry, 62 (4), 231–260 (1990)).

From the above point of view, Suzuki et al studied the influence of various ganglioside derivatives on the activity of influenzasialidase, and obtained interesting results (Suzuki et al, Glycoconjugate J., 7 (1990)).

Such a compound that is bound with the virussialidase strongly but does not act as a substrate is extremely useful in the analysis of a three-dimensional active center structure of this enzyme, and also expected to open a new way for preventing virus infection.

The sialic acid moiety which is partially acetylated in the ganglioside is protected against the function of sialidase, and assumed to be a factor which will cause a carcinomatous change on antigenicity of human melanoma and a change on the antigenicity of cytopolysaccharide. Further, the partially acetylated sialic acid residue may have an important function in the bonding of the ganglioside with the virus.

Sialic acid is a collective name of a group of neuramic acid derivatives, and has acetyl or glycolyl groups as substituents of amino groups, and an acetyl, lactyl, phosphate ester, sulfate ester or methyl group as a substituent of a hydroxyl group. Today, 30 sialic acids are found, and their chemical structures have been determined.

In addition, it is found that the ganglioside takes part in the mechanisms of proliferation and metastasis of cancer cells. That is, the natural ganglioside GM3 has a property to suppress the proliferation of cells, and it is desired to selectively exercise this function on the cancer cells. Since the adhesion of the cancer cells to endothelial cells in blood vessels and exudation of the cancer cells outside the blood vessels are caused by the function of the ganglioside in the cancer metastasis, it is desired to provide a medical agent which prevents the metastasis.

The major functions of the sialic acid are 1) charging negative charge to complex carbohydrates, and cell membranes; 2) influence on a conformation of the glycolipids and glycoproteins; 3) information transfer; 4) masking of antigen sites; and the like, and increasing interest will be given to the functions of sialic acid.

As explained above, the gangliosides take part in various life phenomena as the functional molecule. Among the constitutive components of the ganglioside, sialic acid is assumed to have a large influence on the expression of activities thereof.

As seen from the above descriptions, sialic acid is one of the important constitutive components of the ganglioside which contributes to the various life phenomena. Then, it will be necessary to synthesize various gangliosides comprising organic chemically modified sialic acid in order to study the influence of the structure of sialic acid on the expression of the activities thereof, and it is desired to clarify the functions of the gangliosides in the molecule level using the synthesized compounds.

SUMMARY OF THE INVENTION

An object of the present invention is to provide a ganglioside GM3 derivative which has a fluorine atom in its sialic acid group.

Another object of the present invention is to provide an intermediate which is useful in the preparation of such a ganglioside GM3 derivative.

According to the first aspect, the present invention provides a ganglioside GM3 derivative of the formula (I):

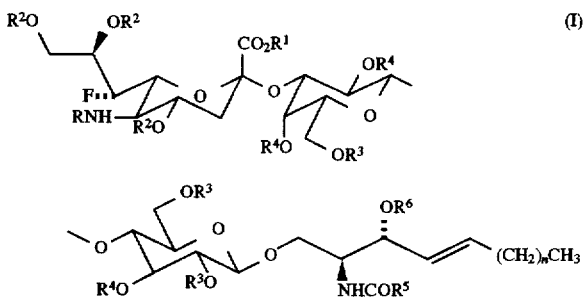

wherein R is an aliphatic acyl group, $R^1$ is a hydrogen atom or a lower alkyl group, $R^2$, $R^3$, $R^4$ and $R^6$ represent independently of one another a hydrogen atom, an aliphatic lower acyl group or an aromatic acyl group, $R^5$ is an straight or branched, saturated or unsaturated aliphatic hydrocarbon group having 1 to 30 carbon atoms, and n is an integer of 0 to 20, provided that when $R^1$ is a hydrogen atom, $R^2$, $R^3$, $R^4$ and $R^6$ are hydrogen atoms, or when $R^1$ is a lower alkyl group, $R^2$, $R^3$, $R^4$ and $R^6$ are each an aliphatic lower acyl group or an aromatic acyl group.

According to the second aspect, the present invention provides an intermediate of the compound of the above formula (I), which is represented by the formula (II):

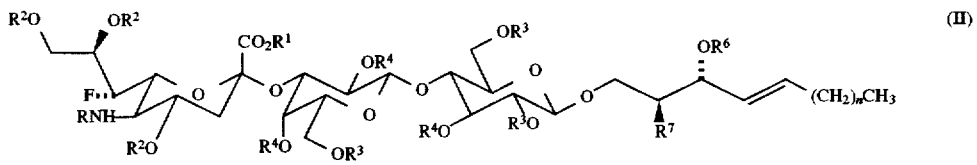

(II)

wherein $R^7$ is a $N_3$ group or a $NH_2$ group, and R, $R^1$, $R^2$, $R^3$, $R^4$, $R^6$ and n are the same as defined above.

According to the third aspect, the present invention provides an intermediate of the compound of the above formula (II), which is represented by the formula (III):

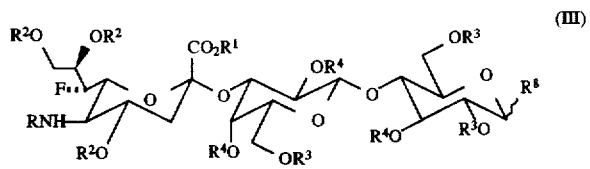

(III)

wherein R is an aliphatic acyl group, $R^1$ is a hydrogen atom or a lower alkyl group, $R^2$, $R^3$ and $R^4$ represent independently of each other a hydrogen atom or an aliphatic or aromatic acyl group, and $R^8$ is a hydroxyl group, a fluorine atom or a —OC(=NH)CCl$_3$ group, provided that when $R^8$ is a fluorine atom or a —OC(=NH)CCl$_3$ group, $R^2$, $R^3$ and $R^4$ are each an aliphatic acyl or aromatic acyl group.

According to the fourth aspect, the present invention provides an intermediate of the compound of the above formula (III), which is represented by the formula (IV):

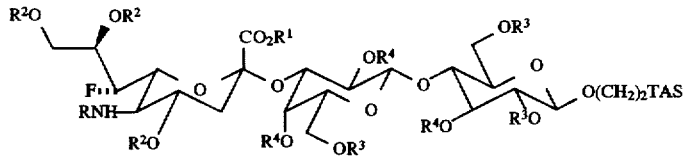

(IV)

wherein R is an aliphatic acyl group, $R^1$ is a hydrogen atom or a lower alkyl group, $R^2$, $R^3$ and $R^4$ represent independently of each other a hydrogen atom or an aliphatic or aromatic acyl group, and TAS represents a trialkylsilyl group.

DETAILED DESCRIPTION OF THE INVENTION

Herein, the lower alkyl group means an alkyl group having 1 to 4 carbon atoms. The aliphatic lower acyl group or aliphatic acyl group means an aliphatic acyl group having 1 to 4 carbon atoms, and the aromatic acyl group means an aromatic acyl group having 7 to 9 carbon atoms. In the trialkylsilyl group, each alkyl group has 1 to 4 carbon atoms.

As understood from the above chemical structure of the formula (I), the fluorine-substituted ganglioside GM3 derivative of the present invention consists of a sialic acid derivative moiety, a lactose moiety, and a ceramide moiety, and is a derivative in which the hydroxyl group at the 7-position of the sialic acid is replaced by the fluorine atom.

This ganglioside GM3 derivative can be prepared by reaction steps comprising firstly synthesizing a thioalkyl compound of the fluorine-containing sialic acid derivative, condensing this thioalkyl compound with a 2,6,6'-triacyl derivative of lactose to obtain a sialyllactose derivative, and then introducing a ceramide moiety.

Hereinafter, the preparation method of the fluorine-substituted ganglioside GM3 derivative of the present invention will be explained.

As a starting compound in the preparation of the fluorine-substituted ganglioside GM3 derivative (I) of the present invention, for example, 7-deoxy-7-fluoro-N-acetyl-neuraminic acid is used. This compound is easily synthesized according to the process described in, for example, WO95/32955 and EP-A-0 711 766. That is, hydroxyl groups of N-acetyl-D-galactosamine except the hydroxyl group on the 4-position are protected, while a fluorine atom is introduced to the hydroxyl group on the 4-position at the same time as the Walden inversion, and N-acetyl-4-deoxy-4-fluoro-D-glucosamine is obtained. Then, this compound is subjected to an aldol reaction with pyruvic acid using an enzyme (N-acetyl-neuraminic acid aldolase) at the same time as isomerization to synthesize desired 7-deoxy-7-fluoro-N-acetyineuraminic acid, which is separated with ion exchange resins.

By esterifying the carboxylic acid moiety at the 1-position of the above obtained compound with an alcohol, a compound of the formula (V-1):

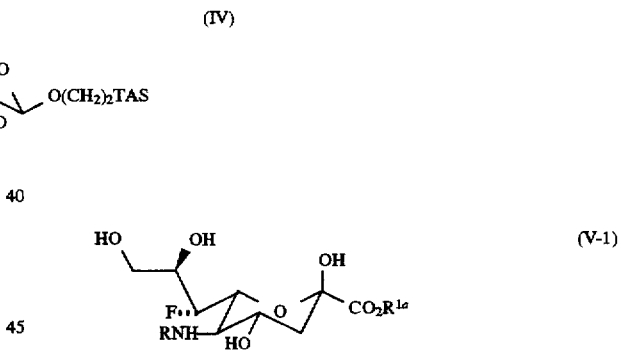

(V-1)

wherein R is an aliphatic lower acyl group, and $R^{1a}$ is a lower alkyl group is obtained.

The esterification is performed as follows:

For example, in the case of a methyl ester, the above starting compound and a cation exchange resin ($H^+$ type), which has been dried overnight in a vacuum desiccator containing diphosphorus pentoxide and potassium hydroxide, are added to anhydrous methanol, and reacted at room temperature for 1 to 6 hours, preferably 2 to 3 hours while stirring, followed by the removal of the ion exchange resin by filtration. The filtrate is concentrated to obtain the esterified compound.

Then, the compound of the above formula (V-1) is reacted with an acyl halide of the formula:

$$R^{2a}X$$

wherein $R^{2a}$ is an aliphatic lower acyl group or an aromatic acyl group, and X is a halogen atom (e.g. acetyl chloride), at about 35° C. Thus, the hydroxyl groups at the 4, 8 and 9-positions are converted to acetoxy groups, while the OH group at the 2-position is converted to the halogen atom, and a compound of the formula (V-2):

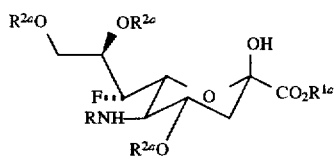

wherein $R^{2a}$ is an aliphatic lower acyl group or an aromatic acyl group, X is a halogen atom, and R and $R^{1a}$ are the same as defined above is obtained.

Next, the compound of the above formula (V-2) is dissolved in anhydrous dichloromethane, and then thioacetic acid and potassium thioacetate are added to the solution while cooling on an ice bath, and reacted at room temperature. Thus, the halogen atom at the 2-position is thioacetylated, and a compound of the formula (V-3):

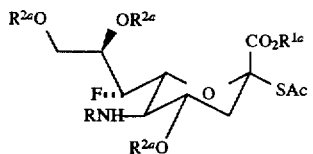

wherein Ac represents an acetyl group, and R, $R^{1a}$ and $R^{2a}$ are the same as defined above is obtained.

The compound of the formula (V-3) is reacted with an alkali metal alkoxide such as sodium methoxide in an alcoholic solvent at a low temperature, followed by the removal of the solvent to obtain a compound of the formula (V-4):

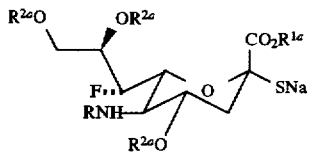

wherein R, $R^{1a}$ and $R^{2a}$ are the same as defined above. This compound is then reacted with an alkyl iodide such as methyl iodide in a suitable aprotic solvent such as dimethylformamide at room temperature or a temperature between 25° and 35° C., followed by post-treatment by a conventional method to obtain a thioalkyl compound of the sialic acid derivative of the formula (V-5):

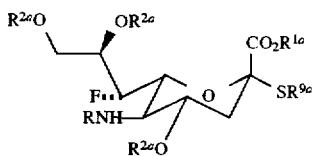

wherein $R^{9a}$ is a lower alkyl group, and R, $R^{1a}$ and $R^{2a}$ are the same as defined above.

Then, the above prepared thioalkyl compound of the sialic acid derivative is condensed with the 2,6,6'-triacyl compound of lactose of the formula (VI):

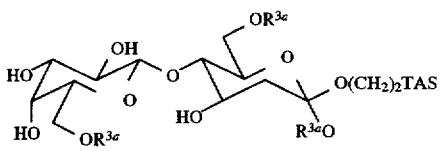

wherein $R^{3a}$ is an aliphatic lower acyl group or an aromatic acyl group, and TAS represents a trialkylsilyl group.

The compound of the formula (VI) can be easily synthesized by the process disclosed in JP-A-3-101691. That is, firstly, 2-(trialkylsilyl)ethyl-β-D-lactoside is benzylated only at the 3'-position with di-n-butyltin oxide, tetra-n-butylammonium bromide and benzyl bromide in a nonpolar solvent (e.g. benzene, toluene, chloroform, dichloromethane, etc.), and treated with an acylating agent (e.g. benzoyl chloride, etc.) in the presence of a base such as pyridine while cooling if desired, according to a general method of acylation to selectively acylate the 2-, 6- and 6'-positions, followed by elimination of the benzyl group at the 3'-position only. Thus, the compound of the formula (VI) is obtained.

In the condensation reaction, the thioalkyl compound of the sialic acid of the formula (V-5) and the 2,6,6'-triacyl compound of lactose of the formula (VI) are dissolved in a solvent such as anhydrous propionitrile, activated molecular sieve 4A is added to the solution, and the mixture is stirred overnight under argon atmosphere. Thereafter, the mixture is cooled to a low temperature, and N-iodosuccinimide and then trifluoromethanesulfonic acid are added and reacted at −45° to −40° C. When a condensation promotor such as N-iodosuccinimide and trifluoromethanesulfonic acid in propionitrile is used, a sialyllactose derivative of the formula (IV-1):

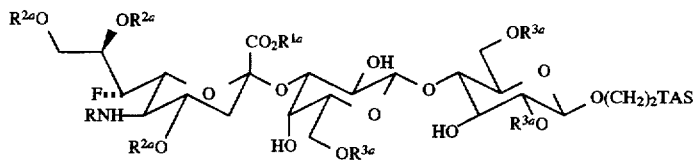

wherein R, $R^{1a}$, $R^{2a}$, $R^{3a}$ and TAS are the same as defined above is obtained regioselectively and stereoselectively.

The free hydroxyl groups of the obtained sialyl lactose derivative are acylated and protected to obtain a compound of the formula (IV-2):

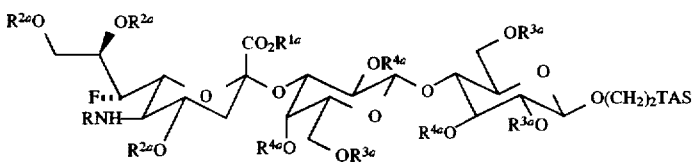

wherein $R^{4a}$ is an aliphatic lower acyl group or an aromatic acyl group, and R, $R^{1a}$, $R^{2a}$, $R^{3a}$ and TAS are the same as defined above.

The acylation can be performed by dissolving the compound of the formula (IV-1) in a solvent, for example, pyridine and reacting the compound with an acyl halide or an acid anhydride at room temperature.

Then, boron trifluoride diethyl etherate is reacted with the compound of the formula (IV-2) to eliminate the $(CH_2)_2TAS$ group at the 1-position, and a compound of the formula (III-1):

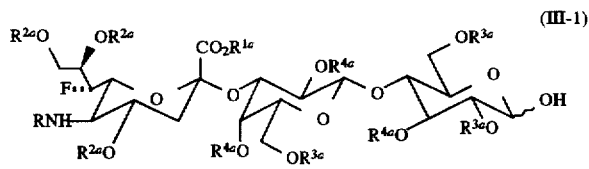

wherein R and $R^{1a}$ to $R^{4a}$ are the same as defined above is obtained.

The elimination of the $(CH_2)_2TAS$ group is performed by dissolving the compound of the formula (IV-2) in dichloromethane, dropwise adding boron trifluoride diethyl etherate to the solution while cooling on an ice bath and reacting them at room temperature under argon atmosphere.

Then, the OH group in the glucose moiety of the compound of the formula (III-1) is activated by changing it to a —OC(=NH)CCl$_3$ group or a fluorine atom.

To obtain a trichloroacetoimidate compound, for example, the compound of the formula (III-1) is dissolved in dichloromethane under argon atmosphere, and trichloroacetonitrile and 1,8-diazabicyclo[5.4.0]undec-7-ene are added to the solution which is cooled at −5° C., and reacted while cooling on an ice bath.

To obtain a fluorinated compound, the compound of the formula (III-1) is reacted with diethylaminosulfur trifluoride are reacted in dichloromethane at a temperature of −10° to 30° C., preferably 0° to 10° C.

By the above steps, a compound of the formula (III-2):

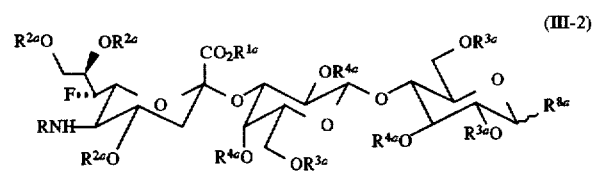

wherein $R^{8a}$ is a —OC(=NH)CCl$_3$ group or a fluorine atom, and R and $R^{1a}$ to $R^{4a}$ are the same as defined above.

Next, the compound of the formula (III-2) is condensed with an azidosphingosine derivative of the formula (VII):

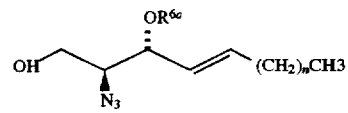

wherein $R^{6a}$ is an aliphatic lower acyl group or an aromatic acyl group, and n is an integer of 0 to 20.

The azidosphingosine derivative may be easily obtained according to the method described in Carbohydrate Research, 202 (1990) 177–191, by synthesizing azidosphingosine, protecting a primary hydroxyl group at the 1-position with a suitable protecting group such as a triphenylmethyl group, also protecting a hydroxyl group at the 3-position with an acyl chloride such as benzoyl chloride by a conventional method, and then removing the protecting group at the 1-position with, for example, boron trifluoride diethyl etherate.

When $R^{8a}$ is the —OC(=NH)CCl$_3$ group, the condensation reaction can be performed by dissolving the compound of the formula (III-2) and the compound of the formula (VII) in dichloromethane, adding activated powdery molecular sieve 4A to the solution, stirring the mixture for 30 minutes under argon atmosphere, dropwise adding boron trifluoride diethyl etherate while cooling with ice, and reacting them at 0° C.

When $R^{8a}$ is a fluorine atom, the condensation reaction can be performed by reacting the compound of the formula (III-2) and the compound of the formula (VII) in dichloromethane in the presence of stannous chloride and silver perchlorate at a temperature of 15° to 25° C.

Accordingly, a compound of the formula (II-1):

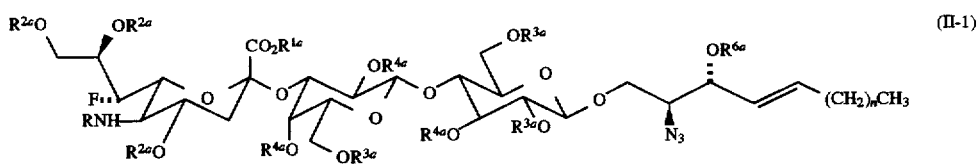

Subsequently, the azido group of this compound is reduced to an amino group in a tributylphosphine or triphenylphosphine/water system or a hydrogen sulfide/pyridine system to obtain a compound of the formula (II-2):

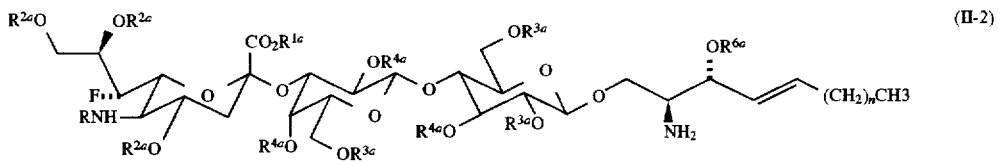

wherein R, $R^{1a}$ to $R^{4a}$, $R^{6a}$ and n are the same as defined above is obtained.

The amino group of the above compound and a carboxyl group of a compound of the formula (VIII):

$$R^{5a}COOH \qquad (VIII)$$

wherein $R^{5a}$ is a straight or branched, saturated or unsaturated aliphatic hydrocarbon group having 1 to 30 carbon atoms are condensed to form an amide bond using a dehydrating agent such as dicyclohexylcarbodiimde (DCC), diisopropylcarbodiimide (DIPC), N-ethyl-N'-3-dimethylaminopropylcarbodiimide (WSCI), etc., and a compound of the formula (I-1):

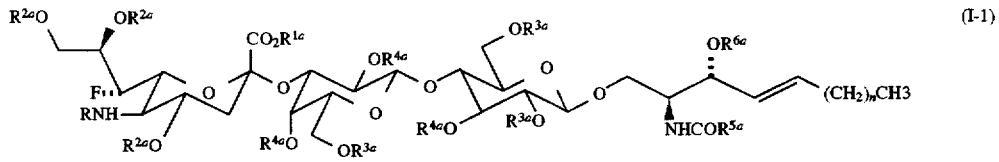

wherein R, $R^{1a}$ to $R^{6a}$ and n are the same as defined above is obtained.

In this reaction, a molar ratio of the compound of the formula (II-2) to the compound of the formula (VIII) is from 1:0.5 to 1:2.0, preferably from 1:1 to 1:1.1. The dehydrating agent is used in an amount of 1 to 2 moles, preferably 1 to 1.1 moles per one mole of the compound of the formula (II-2). Preferred examples of the solvent are dichloromethane, chloroform, dichloroethane, dimethylformamide, and the like. A reaction temperature is usually from 15° to 25° C. After the completion of the reaction, the reaction mixture is subjected to post-treatment such as extraction, evaporation, etc., and the product is purified by column chromatography, if desired.

From the obtained compound of the formula (I-1), the protecting groups of the hydroxyl group and carboxyl group are removed to obtain the ganglioside GM3 derivative of the present invention in which the hydroxyl group at the 7-position of the sialic acid is replaced by the fluorine atom and which is represented by the formula (I-2):

water is added to the mixture and stirred at 0° C. for 1 to 6 hours to eliminate the protecting group of the carboxyl group. After desalting with a $H^+$ type cation exchange resin, the mixture is purified with Sephadex LH-20 to obtain the ganglioside GM3 derivative in which the hydroxyl group at the 7-position of the sialic acid is replaced by the fluorine atom and which is represented by the formula (I-2).

The protecting groups of the hydroxyl group and carboxyl group can be removed from the compounds of the formulas (IV-1), (IV-2), (III-1), (III-2), (II-1) and (II-2) under the same conditions as above.

As explained above, sialic acid is one of the important constitutive components of the gangliosides which contribute to the various life phenomena. Thus, it is useful to synthesize the gangliosides which are organic chemically modified with the fluorine atom in order to study the influence of the structure of sialic acid on the expression of the activities thereof.

The fluorine-substituted gangliosides of the present invention have some functions relating to biological activities such as large resistance to sialidase, and protected from metabolic decomposition, as well as recognition of cells. In addition, they are useful in development and clinical application of practical medicines such as agents for preventing infection, agents for preventing proliferation and metastasis of cancer cells, agents for preventing bonding of leukocytes or cancer cells to a blood vessel wall, and the like.

EXAMPLES

The present invention will be illustrated by Examples, which do not limit the scope of the present invention.

Abbreviations used in the NMR data in Examples have the following meanings:

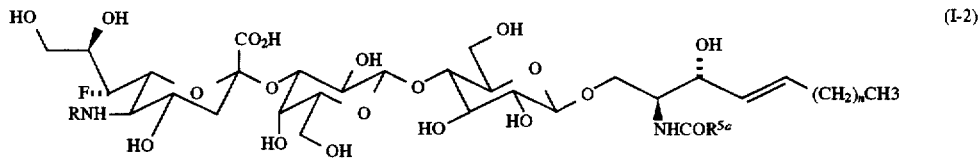

wherein R, $R^{5a}$ and n are the same as defined above.

For example, this reaction may be performed as follows:
The compound of the formula (I-1) is dissolved in anhydrous methanol, and 2 to 4 times equivalents of sodium methoxide is added to the solution, and reacted at a temperature between room temperature and 50° C. for 30 minutes to 10 hours to remove the protecting group of the hydroxyl group. Then, after cooling the mixture to 0° C., Me: Methyl group; Ac: Acetyl group; Ph: Phenyl group.

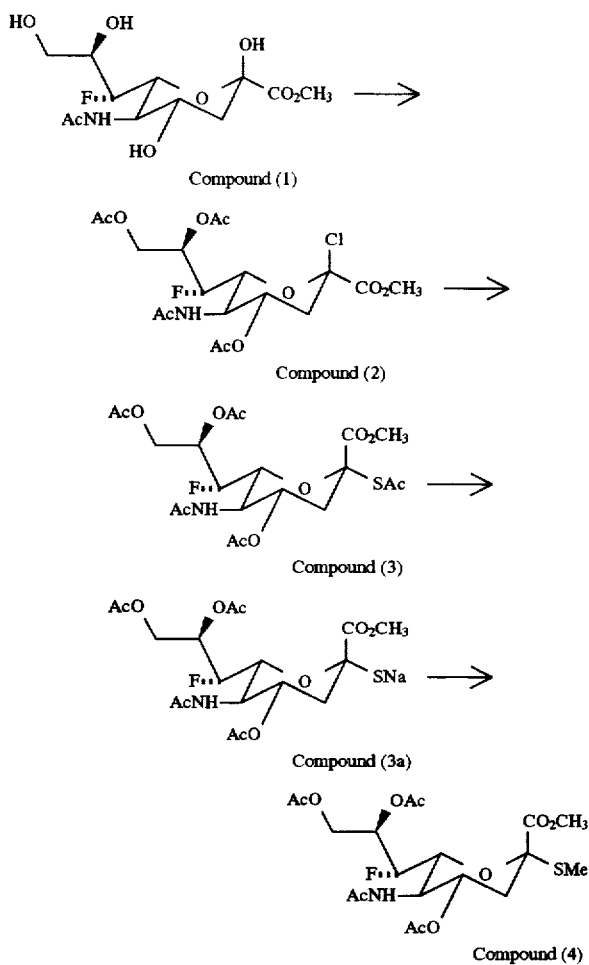

Example 1

Synthesis of methyl (5-acetamide-3,5,7-trideoxy-7-fluoro-D-glycero-β-D-galacto-2-nonulopyranodie)nate (Compound (1))

7-Deoxy-7-fluoro-N-acetylneuraminic acid (0.403 g, 1.30 mmol) was dissolved in anhydrous methanol (40 ml). To the solution, Dowex 50W-X8 (1.211 g), which had been washed with methanol and then dried overnight in a vacuum desiccator in the presence of phosphorus pentoxide and potassium hydroxide, was added, and the mixture was stirred at room temperature for 3 hours under argon atmosphere. After separating the solution by decantation, additional anhydrous methanol (20 ml) was added to the insoluble material, and the mixture was stirred at room temperature for 1.5 hours under argon atmosphere. The solution was filtrated under vacuum, and the residue was washed with methanol. The filtrate, washings and the solution separated by decantation were combined and evaporated to dryness. The residue was refined by silica gel column chromatography (eluent:chloroform:methanol =4:1), and the compound (1) (0.309 g) was obtained. The yield was 73.4%.

$C_{12}H_{20}NO_8F$ (325.29)

$^1$H-NMR (CD$_3$OD; TMS): δ 1.99 (3H, s, NAc), 2.19 (1H, dd, J$_{3e,4}$=4.4 Hz, J$_{3e,3a}$=12.9 Hz, H-3e), 3.78 (3H, s, CO$_2$Me).

$^{19}$F-NMR (CD$_3$OD; CFCl$_3$): δ −207 (dd, 1F, J$_{F,7}$=45.7 Hz, J$_{F,6}$=28.0 Hz, C7-F).

Example 2

Synthesis of methyl (5-acetamide-4,8,9-tri-O-acetyl-2-chloro-3,5,7-trideoxy-7-fluoro-D-glycero-β-D-galacto-2-nonulopyranosid)nate (Compound (2))

The compound (1) (1.12 g, 3.44 mmol) was added to acetyl chloride (55 ml) and stirred at 36° C. for 16 hours while monitoring the progress of the reaction by TLC (developer, chloroform: acetone=7:3). Then, the reaction mixture was concentrated at a temperature of 30° C. or lower under vacuum. The residue was dissolved in anhydrous benzene, followed by concentration under vacuum, and the crude compound (2) (1.60 g) was obtained. The yield was 98.9%.

$C_{18}H_{25}NO_{10}ClF$ (469.86)

[α]$_D$=−58.7° (c=1.0, CHCl$_3$)

IR$^{KBr}_{max}$(cm$^{-1}$): 3700–3150 (NH), 1750 (ester), 1650, 1540 (amide).

$^1$H-NMR (CDCl$_3$; TMS): δ2.07–2.09 (12H, s, 3OAc, NAc), 2.79 (1H, dd, J$_{3e,4}$=4.6 Hz, J$_{3a,3e}$=13.9 Hz, H-3e), 3.87 (3H, s, CO$_2$Me).

$^{19}$F-NMR (CDCl$_3$; CFCl$_3$): δ −211 (ddd, 1F, J$_{F,7H}$=45.7 Hz, J$_{F,6H}$=26.1 Hz, J$_{F,8H}$=10.4 Hz, C7-F).

Example 3

Synthesis of methyl (5-acetamide-4,8,9-tri-O-acetyl-2-S-acetyl-3,5,7-trideoxy-7-fluoro-2-thio-D-glycero-α-galacto-2-nonulopyranosid)nate (Compound (3))

The compound (2) (1.60 g, 3.41 mmol) was dissolved in anhydrous dichloromethane (15 ml). To the solution, potassium thioacetate (1.20 g, 10.5 mmol) and thioacetic acid (0.060 ml, 0.84 mmol) were added, and stirred at room temperature for 18 hours while monitoring the progress of the reaction by TLC (developer, chloroform:methanol= 20:1). Then, the reaction mixture was concentrated under vacuum, and the residue was dissolved in chloroform (10 ml). The solution was washed with a 5% aqueous solution of sodium hydrogencarbonate and then water, and the residue was dried over sodium sulfate. The mixture was filtrated and washed with chloroform. The filtrate and washings were combined, and concentrated under vacuum. The residue was refined by flash chromatography (eluent, chloroform:ethyl acetate=1:1) and further to silica gel column chromatography (eluent, chloroform→chloroform:methanol= 200:1→100:1), and the compound (3) (1.26 g) was obtained. The yield was 73.1%.

$C_{20}H_{28}NO_{11}FS$ (509.52)

$^1$H-NMR (CDCl$_3$; TMS): δ 5.46 (d, 1H, J$_{NH,5}$=9.0 Hz, NH), 4.95 (ddd, 1H, J$_{3e,4}$=4.7 Hz, J$_{4,5}$=10.2 Hz, J$_{3a,4}$=10.8 Hz, H-4), 3.79 (3H, s, CO$_2$Me), 2.60 (1H, dd, J$_{3e,4}$=4.6 Hz, J$_{3a,3e}$=13.0 Hz, H-3e), 2.28 (s, 3H, SAc), 2.05, 2.06, 2.15 (3s, 9H, 3OAc), 1.98 (s, 3H, NAc).

$^{19}$F-NMR (CDCl$_3$; CFCl$_3$): δ −211 (ddd, 1F, J$_{F,7H}$=45.5 Hz, J$_{F,6H}$=26.7 Hz, J$_{F,8H}$=10.9 Hz, C7-F).

Example 4

Synthesis of methyl (methyl 5-acetamide-4,8,9-tri-O-acetyl-3,5,7-trideoxy-7-fluoro-2-thio-D-glycero-α-D-galacto-2-nonulopyranosid)nate (Compound (4))

The compound (3) (0.284 mg, 0.56 mmol) was dissolved in anhydrous methanol (8 ml), and a 0.20N solution of sodium methoxide in methanol (2.5 ml) (0.50 mmol) was dropwise added to the solution at −48° C. and stirred for 5 minutes. Thereafter, the solution was concentrated in vacuo while cooling on an ice water bath, and thoroughly dried. Then, the residue was dissolved in anhydrous dimethylformamide (3 ml). To the solution, methyl iodide (0.050 ml, 0.80 mmol) was added and stirred at room temperature for

13

19 hours and 25 minutes. The residue obtained by concentration under vacuum was refined by column chromatography (eluent, dichloromethane:methanol=200:1→100:1), and the compound (4) (0.231 g) was obtained. The yield was 86.1%.

$C_{19}H_{28}NO_{10}FS$ (481.51)

$[\alpha]_D$=+2.6° (c=0.51, CHCl$_3$)

IR$^{KBr}_{max}$cm$^{-1}$: 3700–3150 (NH), 3150–2800, 1750 (ester), 1650, 1540 (amide).

$^1$H-NMR (CDCl$_3$; TMS): δ 5.45 (dddd, 1H, $J_{8,7}$=9.1 Hz, $J_{9,8}$=4.5 Hz, $J_{8,9'}$=2.4 Hz, $J_{H,F}$=5.2 Hz, H-8), 5.33 (d, 1H, $J_{NH,5}$=9.2 Hz, NH), 4.95 (ddd, 1H, $J_{3e,4}$=4.7 Hz, $J_{4,5}$=10.2 Hz, $J_{3a,4}$=10.8 Hz, H-4), 4.66 (ddd, 1H, $J_{6,7}$=1.0 Hz, $J_{7,8}$=9.1 Hz, $J_{H,F}$=45.6 Hz, H-7), 4.60 (ddd, 1H, $J_{9',8}$=2.4 Hz, $J_{9,9'}$=12.6 Hz, $J_{H,F}$=2.4 Hz, H-9'), 4.20 (ddd, 1H, $J_{4,5}$=$J_{5,6}$=$J_{5,NH}$=10.2 Hz, H-5), 4.17 (ddd, 1H, $J_{9,8}$=4.5 Hz, $J_{9,9'}$= 12.6 Hz, $J_{H,F}$=2.1 Hz, H-9), 3.80 (3H, S, CO$_2$Me), 3.74 (ddd, 1H, $J_{5,6}$=10.7 Hz, $J_{6,7}$=1.0 Hz, $J_{H,F}$=27.2 Hz, H-6), 2.71 (1H, dd, $J_{3e,4}$=4.7 Hz, $J_{3a,3e}$=12.8 Hz, H-3e), 2.06, 2.06, 2.10, 2.15 (4s, 12H, 3OAc, SMe), 1.97 (s, 3H, NAc).

$^{19}$F-NMR (CDCl$_3$; CFCl$_3$): δ –211 (ddd, 1 F, $J_{F,7H}$=45.6 Hz, $J_{F,6H}$=27.2 Hz, $J_{F,8H}$=5.2 Hz, C7-F).

14

MS: m/z (for $C_{19}H_{28}NO_{10}FS$), calculated: 482.150 (M$^+$H), found 482.150.

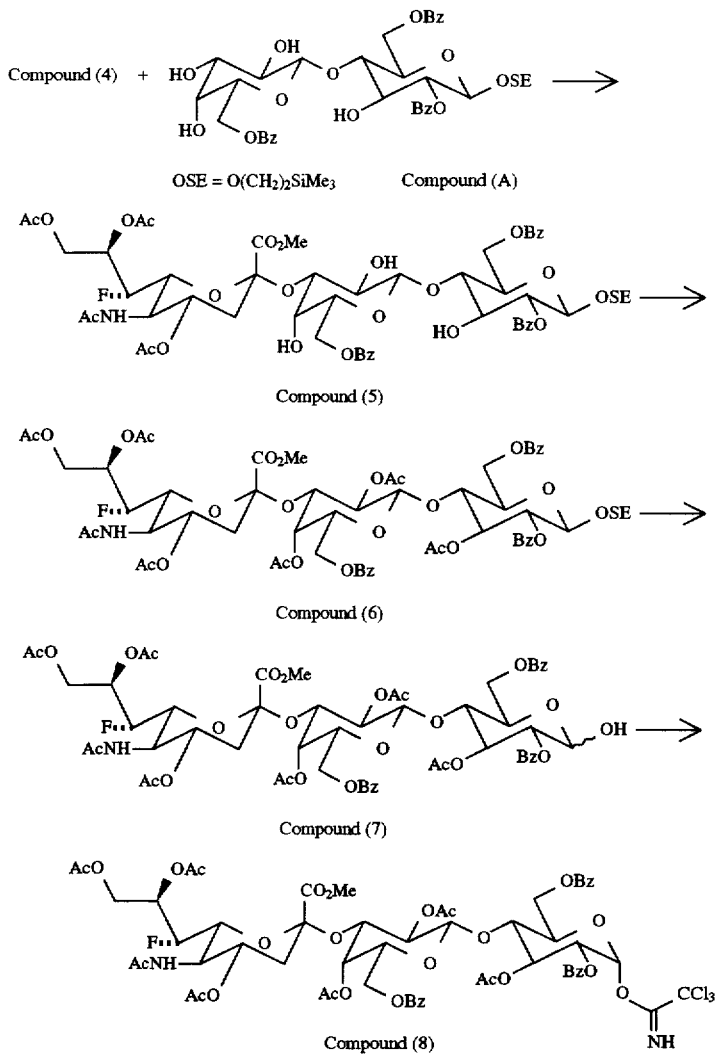

Reaction Scheme 2

Example 5

Synthesis of 2-(trimethylsilyl)ethyl O-(methyl 5-acetamide-4,8,9-tri-O-acetyl-3,5,7-trideoxy-7-fluoro-D-glycero-α-D-galacto-2-nonulopyranosylonate)-(2 3)-O-(6-O-benzoyl-β-D-galactopyranosyl)-(1→4)-2,6-di-O-benzoyl-β-D-glucopyranoside (Compound (5))

The compound (4) (1.107 g, 2.300 mmol) and 2-(trimethylsilyl)ethyl O-(6-O-benzoyl-β-D-galactopyranosyl)-(1→4)-2,6-di-O-benzoyl-β-D-glucopyranoside (Compound (A)) (0.8732 g, 1.157 mmol) were dissolved in anhydrous acetonitrile (11.5 ml) under argon atmosphere. To the solution, powder molecular sieve 4A (2.538 g), which had been dried at 180° C. for 6 hours, was added and stirred at room temperature for 16 hours and 30 minutes. After cooling the mixture to −46° C., N-iodosuccinimide (1.5672 g) and trifluoromethanesulfonic acid (31 µl) were added to the mixture, and stirred at a temperature between −40° and −35° C. for 6 hours and 40 minutes. The reaction mixture was diluted with chloroform and filtrated through celite. The filtrate was washed with a 5% aqueous solution of sodium hydrogencarbonate and then water, and dried over anhydrous magnesium sulfate. Then, the mixture was concentrated under vacuum, and the residue was refined by the column chromatography (eluent, chloroform:methanol = 100:1→90:1→80:1→70:1→60:1→50:1→40:1→5:1) to obtain the crude compound (5) (0.906 g).

The crude compound (5) was again refined by the column chromatography (eluent, ethyl acetate:n-hexane=4:1), and the compound (5) (0.530 g) was obtained. The yield was 38.6%. $C_{56}H_{70}NO_{24}FSi$ (1188.25)

$^1$H-NMR (CDCl$_3$; TMS):

Lactose unit: δ 0.84 (m, 2H, Me$_3$SiCH$_2$CH$_2$O), 3.56 (dt, 1H, J=6.3, 10.0 Hz, Me$_3$SiCH$_2$CH$_2$O), 4.56 (d, 1H, $J_{1',2}$=7.8 Hz, H-1'), 4.62 (d, 1H, $J_{1,2}$=8.0 Hz, H-1), 4.93 (dd, 1H, $J_{6,5}$=1.7 Hz, $J_{gem}$=11.9 Hz, H-6), 5.24 (dd, 1H, $J_{2,1}$=8.0 Hz, $J_{2,3}$=9.6 Hz, H-2), 7.28–8.05 (m, 15 H, 3Bz).

Sialic acid unit: δ 1.94 (s, 3H, AcN), 2.01, 2.02, 2.04 (3s, 9H, 3AcO), 2.66 (dd, 1H, $J_{3e,3a}$=13.1 Hz, $J_{3e,4}$=4.6 Hz, H-3e), 3.78 (s, 3H, MeO), 5.04 (dt, 1H, $J_{4,3e}$=4.6 Hz, $J_{4,3a}$=$J_{4,5}$=10.8 Hz, H-4).

$^{19}$F-NMR (CDCl$_3$; CFCl$_3$): δ −210.7 (ddd, 1F, $J_{F,7H}$=45.6 Hz, $J_{F,6H}$=25.2 Hz, $J_{F,8H}$=8.0 Hz, C7-F).

Example 6

Synthesis of 2-(trimethylsilyl)ethyl O-(methyl 5-acetamide-4,8,9-tri-O-acetyl-3,5,7-trideoxy-7-fluoro-D-glycero-α-D-galacto-2-nonulopyranosylonate)-(2-3)-O-(2, 4-di-O-acetyl-6-O-benzoyl-β-D-galactopyranosyl)-(1→4)-3-O-acetyl-2,6-di-O-benzoyl-β-D-glucopyranoside (Compound (6))

The compound (5) (0.085 g, 0.0715 mmol) was dissolved in anhydrous pyridine (4.6 ml). After cooling on an ice water bath, the acetic anhydride (2.3 ml) was added to the solution, and stirred at room temperature for 18 hours and 30 minutes. Then, the reaction mixture was concentrated under vacuum, and the residue was refined by the flash chromatography (eluent, ethyl acetate n-hexane=5:1) to obtain the crude compound (6) (0.089 g). The yield was 94.7%.

$C_{62}H_{76}NO_{27}FSi$ (1314.36)

$[α]_D$=+5.12° (c=1.00, CHCl$_3$).

$^1$H-NMR (CDCl$_3$:CD$_3$OD=1:1; TMS):

Lactose unit: δ 0.86 (m, 2H, Me$_3$SiCH$_2$CH$_2$O), 3.60, 3.96 (dt, 1H, J=6.3, 10.0 Hz, Me$_3$SiCH$_2$CH$_2$O), 4.14 (t, 1H, $J_{4,3}$=$J_{4,5}$=9.5 Hz, H-4), 4.61 (dd, 1H, $J_{3',2}$=10.1 Hz, $J_{3',4}$=3.4 Hz, H-3'), 4.75 (d, 1H, $J_{1,2}$=8.0 Hz, H-1), 4.90 (d, 1H, $J_{1',2}$=8.0 Hz, H-1'), 4.98 (dd, 1H, $J_{2',1}$=8.0 Hz, $J_{2',3}$=10.1 Hz, H-2'), 5.04 (dd, 1H, $J_{4',3}$=3.4 Hz, $J_{4',5}$=10.7 Hz, H-4'), 5.19 (dd, 1H, $J_{2,1}$=8.0 Hz, $J_{2,3}$=9.5 Hz, H-2), 5.47 (t, 1H, $J_{3,2}$=$J_{3,4}$=9.5 Hz, H-3), 7.40–8.08 (m, 15H, 3Bz).

Sialic acid unit: δ 1.56 (t, 1H, $J_{3a,3e}$=$J_{3a,4}$=12.3 Hz, H-3a), 1.92, 1.93, 2.02, 2.03, 2.08, 2.12, 2.14 (7s, 21H, AcN, 6AcO), 2.60 (dd, 1H, $J_{3e,3a}$=12.5 Hz, $J_{3e,4}$=4.9 Hz, H-3e), 3.72 (dd, 1H, $J_{6,5}$=10.1 Hz, $J_{6,7F}$=27.1 Hz, H-6), 3.75 (s, 3H, MeO), 4.00 (q, 1H, $J_{5,4}$=$J_{5,6}$=$J_{5,NH}$=6.5 Hz, H-5), 4.12 (ddd, 1H, $J_{9,8}$=4.8 Hz, $J_{9,9'}$=12.6 Hz, $J_{9,7F}$=1.9 Hz, H-9), 4.70 (ddd, 1H, $J_{7,6}$=1.6 Hz, $J_{7,8}$=9.4 Hz, $J_{7,7F}$=46.5 H, H-7), 4.71 (dt, 1H, $J_{9',8}$=$J_{9',7F}$=2.4 Hz, $J_{9',9}$=12.6 Hz, H-9'), 5.67 (ddt, 1H, $J_{8,7}$=9.4 Hz, $J_{8,9'}$=$J_{8,7F}$=4.8 Hz, $J_{8,9}$=2.4 Hz, H-8).

$^{19}$F-NMR (CDCl$_3$:CD$_3$OD=1:1; CFCl$_3$): δ −207.9 (ddd, 1F, $J_{F,7H}$=46.5 Hz, $J_{F,6H}$=27.1 Hz, $J_{F,8H}$=4.8 Hz, C7-F).

Example 7

Synthesis of O-(methyl 5-acetamide-4,8,9-tri-O-acetyl-3, 5,7-trideoxy-7-fluoro-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-β-D-glucopyranoside (Compound (7))

The compound (6) (0.1719 g, 0.131 mmol) was dissolved in anhydrous dichloromethane (2.7 ml), and boron trifluoride diethyl etherate (130 μl, 1.06 mmol) was dropwise added to the solution while cooling on an ice bath. Then, the solution was stirred at room temperature (24.7° C.) for 1 hour and 45 minutes, and then at 17°–18° C. for 4 hours and 35 minutes while monitoring the progress of the reaction by TLC (developer, chloroform:methanol=15:1). The reaction mixture was diluted with dichloromethane, and washed with a 1M aqueous solution of sodium hydrogencarbonate and then water. The mixture was dried over anhydrous sodium sulfate overnight and filtrated, and the filtrate was concentrated under vacuum. The residue was refined by the column chromatography (eluent, chloroform:methanol= 200:1→150:1→100:1→80:1→60:1), and the compound (7) (0.1107 g) and crude compound (7) (0.0392 g) were obtained. The crude compound was again refined by the column chromatography (eluent:ethyl acetate:chloroform= 3:1) to obtain the compound (7) (0.0253 g). The yield was 85.6%.

$C_{57}H_{64}NO_{27}F$ (1214.12)

$[α]_D$=+32.80 (c=1.04, CHCl$_3$).

$IR^{KBr}_{max}$cm$^{-1}$: 3700–3150 (OH, NH), 1750, 1230 (ester), 1540 (amide), 1450, 1370 (CH$_3$), 715 (phenyl).

MS: m/z (for $C_{57}H_{64}NO_{27}F$), calculated: 1214.37280 (M+H), found: 1214.37573.

Example 8

Synthesis of O-(methyl 5-acetamide-4,8,9-tri-O-acetyl-3, 5,7-trideoxy-7-fluoro-D-glycero-α-D-galacto-2-nonulopyranosylonate)-(2→3)-O-(2,4-di-O-acetyl-6-O-benzoyl-β-D-galactopyranosyl)-(1→4)-3-O-acetyl-2,6-di-O-benzoyl-α-D-glucopyranosyl trichloroacetoimidate (Compound (8))

The compound (7) (0.2089 g, 0.1721 mmol) was dissolved in anhydrous dichloromethane (1.3 ml), and trichloroacetonitrile (0.52 ml, 5.19 mmol) and 1,8-diazabicyclo [5.4.0]undec-7-ene (0.014 ml, 0.094 mmol) were added to the solution at −9.1° C. After allowing the mixture to warm, the mixture was stirred between −3° C. and +2° C. The residue obtained by concentration under vacuum was refined by the column chromatography (eluent, chloroform→chloroform:methanol=100:1→80:1), and the compound (8) (0.2240 g) was obtained. The yield was 95.8%.

$C_{59}H_{64}N_2O_{27}FCl_3$ (1358.51)

$[α]_D$=+33.3° (c=0.77, CHCl$_3$).

$IR^{KBr}_{max}$cm$^{-1}$: 3390 (NH), 1750, 1230 (ester), 1680, 1540 (amide), 1450, 1370 (CH$_3$), 710 (phenyl).

$^1$H-NMR (CDCl$_3$; TMS):

Lactose unit: δ 3.98 (m, 1 H, H-6), 4.16 (t, 1 H, $J_{4,3}$=$J_{4,5}$=9.8 Hz, H-4), 4.38 (dd, 1H, $J_{5,4}$=9.8 Hz, $J_{5,6}$=11.2 Hz, H-5), 4.56 (dd, 1H, $J_{3',2}$=10.1 Hz, $J_{3',4}$=2.7 Hz, H-3'), 4.84 (dd, 1H, $J_{4',3}$=2.7 Hz, $J_{4',5}$=12.1 Hz, H-4'), 4.89 (d, 1H, $J_{1,2}$=8.0 Hz, H-1'), 5.05 (dd, 1H, $J_{2',1}$=8.0 Hz, $J_{2',3}$=10.1 Hz, H-2'), 5.27 (dd, 1H, $J_{2,1}$=3.8 Hz, $J_{2,3}$=9.8 Hz, H-2), 5.83 (t, 1H, $J_{3,2}$=$J_{3,4}$=9.8 Hz, H-3), 6.66 (d, 1H, $J_{1,2}$=3.8 Hz, H-1), 7.38–8.06 (m, 15H, 3Ph), 8.53 (s, 1H, C=NH).

Sialic acid unit: δ 1.64 (t, 1H, $J_{3a,3e}$=$J_{3a,4}$=12.4 Hz, H-3a), 2.58 (dd, 1H, $J_{3e,3a}$=12.4 Hz, $J_{3e,4}$=4.8 Hz, H-3e), 3.66 (dd, 1H, $J_{6,5}$=10.5 Hz, $J_{6,7}$=1.6 Hz, $J_{6,7F}$=27.4 Hz, H-6), 3.73 (s, 3H, MeO), 3.96 (q, 1H, $J_{5,4}$=$J_{5,6}$=$J_{5,NH}$=10.5 Hz, H-5), 4.09 (ddd, 1H, $J_{9,8}$=4.5 Hz, $J_{9,9'}$=12.6 Hz, $J_{9,7F}$=1.9 Hz, H-9), 4.69 (ddd, 1H, $J_{7,6}$=1.6 Hz, $J_{7,8}$=9.2 Hz, $J_{7,7F}$=46.2 Hz, H-7), 4.71 (dt, 1H, $J_{9',8}$=$J_{9',9}$=12.6 Hz, $J_{9',7F}$=2.2 Hz, H-9'), 5.32 (d, 1H, $J_{NH,5}$=10.5 Hz, NH), 5.61 (m, 1H, H-8).

Acetyl unit: δ 1.91, 1.93, 2.02, 2.03, 2.04, 2.09, 2.11 (7s, 21H, AcN, 6AcO).

$^{19}$F-NMR (CDCl$_3$; CFCl$_3$): δ −208.15 (ddd, 1F, $J_{F,7H}$=46.2 Hz, $J_{F,6H}$=27.4 Hz, $J_{F,8H}$=6.6 Hz, C7-F).

MS: m/z (for C$_{59}$H$_{64}$N$_2$O$_{27}$FCl$_3$), calculated: 1379.26441 (M+Na)$^+$; found: 1379.26725.

raphy (eluent, ethyl acetate : n-hexane=3:2) to obtain the compound (9) (0.1666 g). The yield was 67.8%.

C$_{82}$H$_{101}$N$_4$O$_{29}$F (1625.71)

|α|$_D$=−9.6° (c=0.58, CHCl$_3$).

IR$^{KBr}_{max}$cm$^{-1}$: 2930, 2860 (CH$_2$), 2150 (azide), 1750, 1230 (ester), 1540 (amide), 1450, 1370 (CH$_3$), 712 (phenyl).

$^1$H-NMR (CDCl$_3$; TMS):

Lactose unit: δ 4.10 (t, 1H, $J_{4,3}$=$J_{4,5}$=9.4 Hz, H-4), 4.56 (dd, 1H, $J_{3',2'}$=10.1 Hz, $J_{3',4'}$=3.4 Hz, H-3'), 4.68 (d, 1H, $J_{1,2}$=7.8 Hz, H-1), 4.85 (d, 1H, $J_{1',2'}$=7.9 Hz, H-1'), 5.01

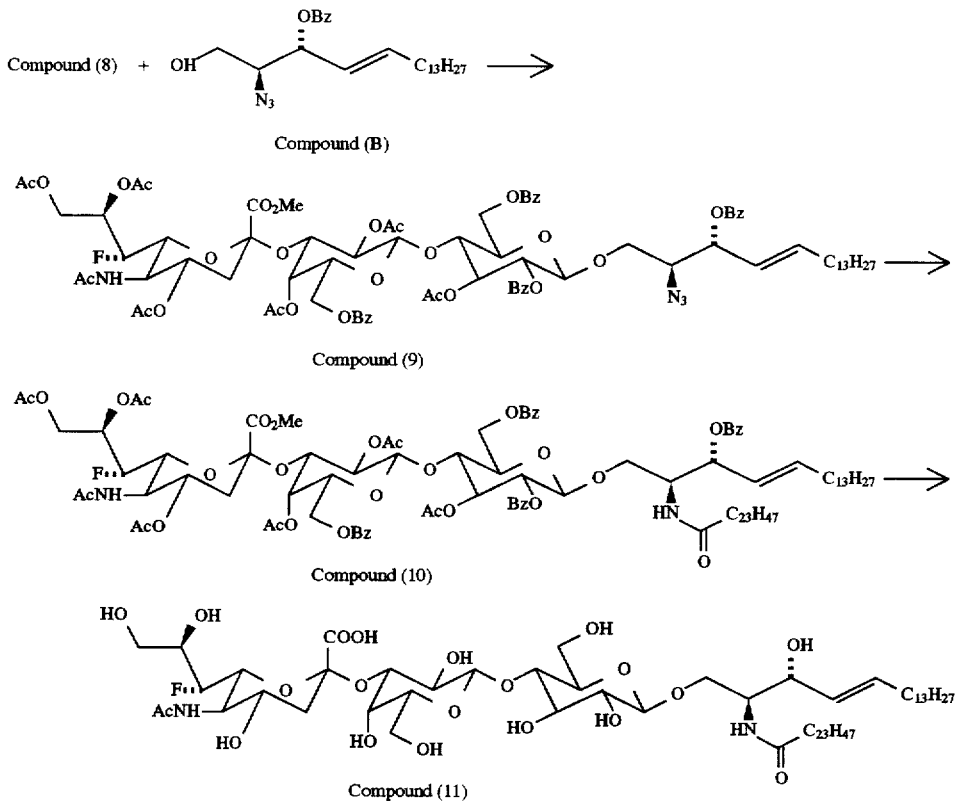

Reaction Scheme 3

Compound (B)

Compound (9)

Compound (10)

Compound (11)

Example 9

Synthesis of O-(methyl 5-acetamide-4,8,9-tri-O-acetyl-3,5,7-trideoxy-7-fluoro-D-glycero-α-D-galacto-2-nonulopyranosylonate)-(2-3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-2-azido-3-O-benzoyl-4-octadecen-1,3-diol (Compound (9))

The compound (8) (0.2052 g, 0.1510 mmol) and (2S,3R,4E)-2-azido-O-benzoyl-4-octadecen-1,3-diol (Compound (B)) (0.1302 g, 0.3031 mmol) were dissolved in dichloromethane (4.2 ml), and molecular sieve 4A (2.564 g), which had been dried at 180° C. for 6 hours in vacuo, was added to the solution and stirred at room temperature for 45 minutes under argon atmosphere. Then, boron trifluoride diethyl etherate (40 μl, 0.325 mmol) was dropwise added to the mixture while cooling on an ice water bath and stirred for 3 hours and 40 minutes. The reaction mixture was diluted with dichloromethane, and filtrated through celite, and the filtrate was washed with a 1M aqueous solution of sodium hydrogencarbonate and then water, followed by drying over anhydrous sodium sulfate. The residue obtained by concentration under vacuum was refined by the flash chromatog- (dd, 1H, $J_{2',1}$=7.9 Hz, $J_{2',3}$=10.1 Hz, H-2'), 5.25 (dd, 1H, $J_{2,1}$=7.8 Hz, $J_{2,3}$=9.4 Hz, H-2), 5.48 (t, 1H, $J_{3,4}$=$J_{3,2}$=9.4 Hz, H-3).

Sialic acid unit: δ 1.65 (t, 1H, $J_{3a,3e}$=$J_{3a,4}$=12.5 Hz, H-3a), 2.58 (dd, 1H, $J_{3e,3a}$=12.5 Hz, $J_{3e,4}$=4.8 Hz, H-3e), 3.66 (dd, 1H, $J_{6,5}$=9.9 Hz, $J_{6,7}$=1.5 Hz, $J_{6,7F}$=27.1 Hz, H-6), 3.73 (s, 3H, MeO), 3.99 (q, 1H, $J_{5,4}$=$J_{5,6}$=$J_{5,NH}$=9.9 Hz, H-5), 4.65 (ddd, 1H, $J_{7,6}$=1.5 Hz, $J_{7,8}$=9.1 Hz, $J_{7,7F}$=46.2 Hz, H-7), 4.71 (dt, 1H, $J_{9,8}$=$J_{9,9'}$=12.7 Hz, $J_{9',7F}$=2.2 Hz, H-9'), 5.35 (d, 1H, $J_{NH,5}$=9.9 Hz, NH), 5.61 (m, 1H, H-8).

Azidosphingosine unit: δ 0.88 (t, 3H, J=7.0 Hz, Me), 1.3 (m, 24H, CH$_2$), 3.55 (dd, 1H, $J_{1a,1b}$=9.9 Hz, $J_{1a,2}$=5.8 Hz, H-1a), 3.85 (dd, 1H, $J_{1b,1a}$=9.9 Hz, $J_{1b,2}$=5.7 Hz, H-1b), 5.42 (dd, 1H, $J_{4,3}$=8.1 Hz, $J_{4,5}$=15.3 Hz, H-4), 5.51 (dd, 1H, $J_{3,2}$=4.0 Hz, $J_{3,4}$=8.1 Hz, H-3), 5.68 (dt, 1H, $J_{5,4}$=$J_{5,6a}$=15.3 Hz, $J_{5,6b}$=6.8 Hz, H-5).

O-Acyl group: δ 1.93, 1.94, 2.01, 2.03, 2.05, 2.09, 2.10 (7s, 21H, AcN, 6AcO), 7.32–8.10 (m, 20H, 4Ph).

$^{19}$F-NMR (CDCl$_3$; CFCl$_3$): δ −208.15 (ddd, 1F, $J_{F,7H}$=46.2 Hz, $J_{F,6H}$=27.1 Hz, $J_{F,8H}$=6.6 Hz, C7-F).

MS: m/z (for C$_{82}$H$_{101}$N$_4$O$_{29}$F), calculated: 1647.64335 (M+Na)$^+$, found: 1647.64123.

Example 10

Synthesis of O-(methyl 5-acetamide-4,8,9-tri-O-acetyl-3,5,7-trideoxy-7-fluoro-D-glycero-α-D-galacto-2-nonuloypyranosylonate)-(2→3)-O-(2,4-di-O-acetyl-6-O-benzoyl-β-D-galactopyranosyl)-(1→4)-O-(3-O-acetyl-2,6-di-O-benzoyl-β-D-glucopyranosyl)-(1→1)-(2S,3R,4E)-3-O-benzoyl-2-tetracosanamido-4-octadecen-1,3-diol (Compound (10))

The compound (9) (0.1670 g, 0.1027 mmol) was dissolved in a mixed solvent of pyridine and water (=5:1 (v/v)) (20.5 ml) and stirred together with hydrogen sulfide at room temperature for 63 hours and 40 minutes (19 hours and 5 minutes while bubbling hydrogen sulfide and 44 hours and 35 minutes in a closed state), followed by evaporation to dryness under vacuum. The residue was dissolved in anhydrous dichloromethane (8.6 ml), and tetracosanoic acid (0.0769 g, 0.2086 mmol) and 1-ethyl-3-(3-dimethylaminopropyl)carbodiimide hydrochloride (0.0620 g, 0.3234 mmol) were added to the solution, and stirred at room temperature under argon atmosphere for 16 hours and 55 minutes. The mixture was diluted with dichloromethane and washed with water, followed by drying over anhydrous sodium sulfate. The mixture was filtrated, and the filtrate was concentrated under vacuum. The obtained residue was refined by the flash chromatography (eluent, ethyl acetate n-hexane=3:2), the compound (10) (0.1294 g) was obtained. The yield was 64.6%.

$C_{106}H_{149}N_2O_{30}F$ (1950.34)

$[\alpha]_D$=+4.7° (c=2.05, $CHCl_3$).

$IR^{KBr}_{max}cm^{-1}$: 3440 (NH), 2920, 2850 ($CH_2$), 2110 (azide), 1750, 1230 (ester), 1670, 1550 (amide), 1450, 1370 ($CH_3$), 713 (phenyl).

$^1$H-NMR ($CDCl_3$; TMS):

Lactose unit: δ 3.78 (ddd, 1H, $J_{5,4}$=9.5 Hz, $J_{5,6}$=5.5 Hz, $J_{5,6'}$=1.7 Hz, H-5), 4.02 (t, 1H, $J_{4,3}$=$J_{4,5}$=9.5 Hz, H-4), 4.25 (dd, 1H, $J_{6,5}$=5.5 Hz, $J_{6,6'}$=12.1 Hz, H-6), 4.55 (dd, 1H, $J_{3',2'}$=10.3 Hz, $J_{3',4'}$=3.4 Hz, H-3'), 4.59 (d, 1H, $J_{1,2}$=7.9 Hz, H-1), 4.80 (d, 1H, $J_{1',2'}$=8.0 Hz, H-1'), 4.99 (dd, 1H, $J_{2',1}$=8.0 Hz, $J_{2',3}$=10.3 Hz, H-2'), 5.17 (dd, 1H, $J_{2,1}$=7.9 Hz, $J_{2,3}$=9.5 Hz, H-2), 5.46 (t, 1H, $J_{3,2}$=$J_{3,4}$=9.5 Hz, H-3).

Sialic acid unit: δ 1.64 (t, 1H, $J_{3a,3e}$=$J_{3a,4}$=12.6 Hz, H-3e), 2.57 (dd, 1H, $J_{3e,3a}$=12.6 Hz, $J_{3e,4}$=4.8 Hz, H-3e), 3.63 (dd, 1H, $J_{6,5}$=10.0 Hz, $J_{6,7F}$=25.9 Hz, H-6), 3.72 (s, 3H, MeO), 3.99 (q, 1H, $J_{5,4}$=$J_{5,6}$=$J_{5,NH}$=10.0 Hz, H-5), 4.12 (ddd, 1H, $J_{9,8}$=8.2 Hz, $J_{9,9'}$=12.8 Hz, $J_{9',7F}$=2.0 Hz, H-9), 4.69 (ddd, 1H, $J_{7,8}$=9.2 Hz, $J_{7,7F}$=47.4 Hz, H-7), 5.28 (d, 1H, $J_{NH,5}$=10.0 Hz, NH), 5.62 (m, 1H, H-8).

Ceramide unit: δ 0.88 (t, 6H, J=7.0 Hz, 2Me), 1.1–1.3 (m, 60H, $CH_2$), 3.58 (dd, 1H, $J_{1,1}$=10.2 Hz, $J_{1,2}$=4.2 Hz, H-1), 4.39 (m, 1H, H-2), 5.40 (dd, 1H, $J_{4,3}$=7.4 Hz, $J_{4,5}$=15.4 Hz, H-4), 5.51 (t, 1H, $J_{3,2}$=$J_{3,4}$=7.4 Hz, H-3), 5.62 (d, 1H, $J_{NH,2}$=5.6 Hz, NH), 5.76 (dt, 1H, $J_{5,4}$=$J_{5,6}$=15.4 Hz, $J_{5,6}$=7.3 Hz, H-5).

O-Acyl group: δ 1.94, 1.99, 2.02, 2.04, 2.07, 2.10 (6s, 21H, AcN, 6AcO), 7.26–8.10 (m, 20H, 4Ph).

$^{19}$F-NMR ($CDCl_3$; $CFCl_3$): δ −208.21 (ddd, 1 F, $J_{F,7H}$=47.4 Hz, $J_{F,6H}$=25.9 Hz, $J_{F,8H}$=7.1 Hz, C7-F).

MS: m/z (for $C_{106}H_{149}N_2O_{30}F$), calculated: 1972.00772 (M+Na)$^+$, found: 1973.00561.

Example 11

Synthesis of O-(5-acetamide-3,5,7-trideoxy-7-fluoro-D-glycero-α-D-galacto-2-nonulopyranosylonic acid)-(2→3)-O-(β-D-galactopyranosyl)-(1→4)-O-(β-D-glucopyranosyl)-(1→1)-(2S,3R,4E)-2-tetracosanamido-4-octadecen-1,3-diol (Compound (11))

The compound (10) (0.1294 g, 0.0664 mmol) was dissolved in anhydrous methanol (5.5 ml), and sodium methoxide (0.02951 g, 0.546 mmol) was added to the solution while cooling with ice, and stirred at room temperature for 15 hours and 55 minutes. Water (0.55 ml) was added to the solution while cooling on an ice bath, and stirred at room temperature for 5 hours. The reaction mixture was passed through a column containing an ion exchange resin IR-120B (H$^+$) (eluent:methanol), and concentrated under vacuum. The residue was passed through a column containing Sephadex LH-20 (eluent: methanol), followed by concentration under vacuum, and the compound (11) (0.0683 g) was obtained. The yield was 81.2%.

$C_{65}H_{119}N_2O_{20}F$ (1267.66)

$[\alpha]_D$=−7.2° (c=0.53, $CHCl_3$: MeOH=1:1).

$IR^{KBr}_{max}cm^{-1}$: 3350 (OH, NH), 2920, 2850 ($CH_2$), 1640 (carbonyl), 1110 (ester), 1630, 1550 (amide), 1470, 1380 ($CH_3$), 1080 (CF).

$^1$H-NMR ($CDCl_3$: $CD_3OD$=1:2+($CD_3$)$_2$SO; TMS):

Lactose unit: δ 4.18 (d, 1H, $J_{1,2}$=7.8 Hz, H-1), 4.31 (d, 1H, $J_{1,2}$=7.8 Hz, H-1').

Sialic acid unit: δ 1.72 (t, 1H, $J_{3a,3e}$=$J_{3a,4}$=12.2 Hz, H-3a), 1.88 (s, 3H, AcN), 2.66 (d, 1H, J=8.6 Hz, H-3e).

Ceramide unit: δ 0.79 (t, 6H, J=6.9 Hz, 2Me), 2.06 (t, 2H, J=7.7 Hz, $CH_2CH_2CO$), 3.97 (t, 1H, $J_{3,2}$=$J_{3,4}$=7.9 Hz, H-3), 4.08 (dd, 1H, $J_{1,1}$=10.2 Hz, $J_{1,2}$=4.4 Hz, H-1), 5.35 (dd, 1H, $J_{4,3}$=7.9 Hz, $J_{4,5}$=15.4 Hz, H-4), 5.68 (dt, 1H, $J_{5,4}$=$J_{5,6}$=15.3 Hz, $J_{5,6}$=6.7 Hz, H-5).

$^{19}$F-NMR ($CDCl_3$: $CD_3OD$=1:2+($CD_3$)$_2$SO; $CFCl_3$): δ −208.66 (dd, 1F, $J_{F,7H}$=44.7 Hz, $J_{F,6H}$=26.8 Hz, C7-F).

MS: m/z (for $C_{65}H_{119}N_2O_{20}F$), calculated: 1289.823812 (M+Na)$^+$; found: 1289.82188.

What is claimed is:

1. A compound of the formula (I):

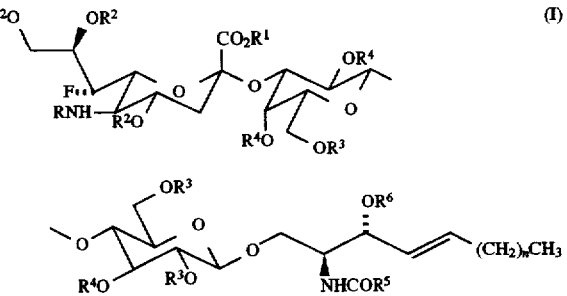

wherein R is an aliphatic acyl group, R$^1$ is a hydrogen atom or a lower alkyl group, R$^2$, R$^3$, R$^4$ and R$^6$ represent independently of one another a hydrogen atom, an aliphatic lower acyl group or an aromatic acyl group, R$^5$ is an straight or branched, saturated or unsaturated aliphatic hydrocarbon group having 1 to 30 carbon atoms, and n is an integer of 0 to 20, provided that when R$^1$ is a hydrogen atom, R$^2$, R$^3$, R$^4$ and R$^6$ are hydrogen atoms, or when R$^1$ is a lower alkyl group, R$^2$, R$^3$, R$^4$ and R$^6$ are each an aliphatic lower acyl group or an aromatic acyl group.

2. A compound of the formula (II):

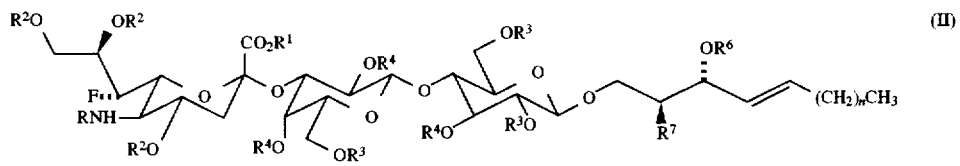

(II)

wherein R is an aliphatic acyl group, $R^1$ is a hydrogen atom or a lower alkyl group, $R^2$, $R^3$, $R^4$ and $R^6$ represent independently of one another a hydrogen atom, an aliphatic lower acyl group or an aromatic acyl group, $R^7$ is a $N_3$ group or a $NH_2$ group, and n is an integer of 0 to 20, provided that when $R^1$ is a hydrogen atom, $R^2$, $R^3$, $R^4$ and $R^6$ are hydrogen atoms, or when $R^1$ is a lower alkyl group, $R^2$, $R^3$, $R^4$ and $R^6$ are each an aliphatic lower acyl group or an aromatic acyl group.

3. A compound of the formula (III):

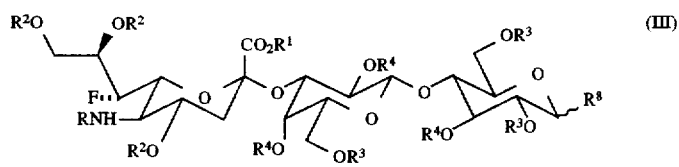

(III)

wherein R is an aliphatic acyl group, $R^1$ is a hydrogen atom or a lower alkyl group, $R^2$, $R^3$ and $R^4$ represent independently of each other a hydrogen atom or an aliphatic or aromatic acyl group, and $R^8$ is a hydroxyl group, a fluorine atom or a —OC(=NH)CCl$_3$ group, provided that when $R^8$ is a fluorine atom or a —OC(=NH)CCl$_3$ group, $R^2$, $R^3$ and $R^4$ are each an aliphatic acyl or aromatic acyl group.

4. A compound of the formula (IV):

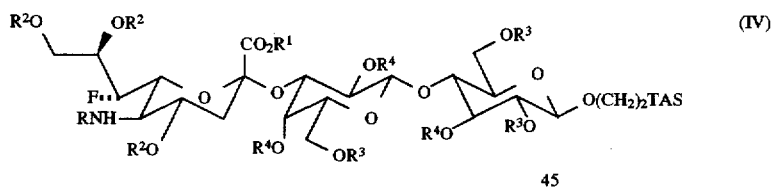

(IV)

wherein R is an aliphatic acyl group, $R^1$ is a hydrogen atom or a lower alkyl group, $R^2$, $R^3$ and $R^4$ represent independently of each other a hydrogen atom or an aliphatic or aromatic acyl group, and TAS represents a trialkylsilyl group.

* * * * *